United States Patent
Wollweber et al.

(10) Patent No.: US 6,194,575 B1
(45) Date of Patent: Feb. 27, 2001

(54) METHOD FOR PRODUCING 1,3-DI-SUBSTITUTED 2-NITROGUANIDINES

(75) Inventors: Detlef Wollweber, Wuppertal; Wolfgang Krämer, Burscheid, both of (DE); Eric Rivadeneira, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/381,669

(22) PCT Filed: Mar. 13, 1998

(86) PCT No.: PCT/EP98/01456

§ 371 Date: Sep. 21, 1999

§ 102(e) Date: Sep. 21, 1999

(87) PCT Pub. No.: WO98/42690

PCT Pub. Date: Oct. 1, 1998

(30) Foreign Application Priority Data

Mar. 25, 1997 (DE) .............................. 197 124 119

(51) Int. Cl.⁷ ................... C07D 277/32; C07D 213/61; C07D 405/06; C07D 417/14

(52) U.S. Cl. ................... 544/180; 544/215; 544/216; 544/224; 544/238; 544/240; 544/241; 544/309; 544/315; 544/319; 544/336; 544/355; 544/405; 546/266; 546/290; 546/332; 548/146; 548/186; 548/205; 548/206; 548/213; 548/225; 548/226; 548/240; 548/243; 549/272

(58) Field of Search ..................................... 544/180, 215, 544/216, 224, 238, 239, 240, 241, 309, 315, 319, 336, 355, 401; 546/290, 295, 266, 332; 548/146, 181, 206, 217, 225, 226, 240, 243, 213, 205, 186; 549/472

(56) References Cited

U.S. PATENT DOCUMENTS

| 4,221,802 | 9/1980 | Durant et al. ..................... 424/273 B |
| 4,804,780 | 2/1989 | Speltz et al. .......................... 564/104 |
| 5,245,040 | 9/1993 | Maienfisch et al. ................. 546/332 |
| 5,783,734 | 7/1998 | Gallenkamp et al. ............... 564/108 |

FOREIGN PATENT DOCUMENTS

| 2052731 | 4/1992 | (CA) . |
| 0 376 279 | 5/1993 | (EP) . |
| 0 383 091 | 11/1993 | (EP) . |
| 0 386 565 | 1/1994 | (EP) . |
| 0 428 941 | 5/1995 | (EP) . |
| 0 375 907 | 1/1996 | (EP) . |
| 3-291267 | 12/1991 | (JP) . |

OTHER PUBLICATIONS

Chemical Abstracts, vol. 116, No. 23, Aug. 6, 1992, Abstract No. 235455, Preparation of substituted nitroguanidines as insecticides.

J. Am. Soc. 76, Apr. 5, 1954, p. 1877–1879, The Preparation and Reactions of 2–Alkyl–1(or 3)–nitro–2–thiopseudourea. Part I. Reaction with Amines, by Lawrence Fishbein & John A. Gallaghan.

*Primary Examiner*—Mukund J. Shah
*Assistant Examiner*—Venkataraman Balasubramanian
(74) *Attorney, Agent, or Firm*—Joseph C. Gil

(57) ABSTRACT

The present invention relates to a process for the preparation of compounds of the formula (I)

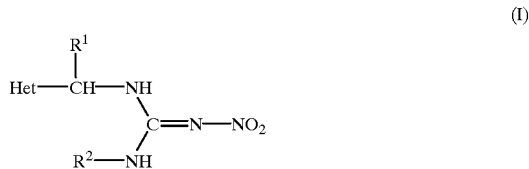

by reacting compounds of the formula (II)

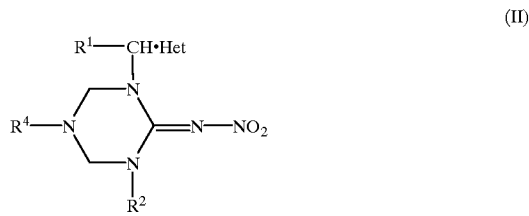

in which

Het, $R^1$, $R^2$ and $R^4$ are as defined in the description, with urea.

9 Claims, No Drawings

METHOD FOR PRODUCING 1,3-DI-SUBSTITUTED 2-NITROGUANIDINES

The present invention relates to a novel type of process for the preparation of 1,3-disubstituted 2-nitroguanidines.

EP-A-0 483 062 discloses a process for the preparation of 1,3-disubstituted 2-nitroguanidines. They are obtained by hydrolysis of corresponding 2-nitroimino-1,3,5-triazacyclohexane derivatives. The hydrolysis is preferably carried out in the presence of strong mineral acids or organic acids.

Disadvantages of this process are the long reaction times and the formation of secondary products, which make it necessary to subject the desired end-products to a complex cleaning operation.

Moreover, as is known, when working in the presence of strong acids, measures must be taken to protect, for example the reactors, from corrosion.

JP-03 291 267 relates to a similar process.

The object of the present invention was to provide a further process for the preparation of 1,3-disubstituted 2-nitroguanidines.

The present invention provides a process for the preparation of compounds of the formula (I)

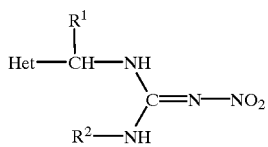

(I)

in which $R^1$ is hydrogen or $C_1$–$C_4$-alkyl, $R^2$ is hydrogen, $C_1$–$C_6$-alkyl, $C_3$–$C_6$-cycloalkyl or a radical —$CH_2R^3$, $R^3$ is $C_2$–$C_5$-alkenyl, $C_2$–$C_5$-alkinyl, phenyl, cyanophenyl, nitrophenyl, halogenophenyl having from 1 to 3 halogen atoms, phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms, 3-pyridyl, 5-thiazolyl, 5-thiazolyl substituted by one to two (preferably one) substituents from the group consisting of $C_1$–$C_3$-alkyl, $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_1$–$C_3$-alkoxy, $C_2$–$C_3$-halogenoalkenyl and $C_2$–$C_3$-halogenoalkinyl having in each case from 1 to 4 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy and halogenoallylthio having in each case from 1 to 3 halogen atoms, halogen, cyano and nitro; or 3-pyridyl substituted by one to four (preferably one or two) radicals from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl and $C_2$–$C_3$-halogenoalkinyl having in each case from 1 to 4 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy and halogenoallylthio having in each case from 1 to 3 halogen atoms, cyano, nitro, $C_1$–$C_3$-alkyl, $C_1$–$C_3$-alkoxy and halogen, Het is an unsubstituted or substituted aromatic or non-aromatic, monocyclic or bicyclic heterocyclic radical, preferably from the series

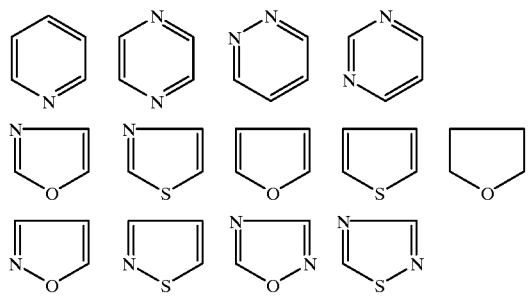

which may include one or two substituents from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl and $C_2$–$C_3$-halogenoalkinyl having in each case from 1 to 4 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy and halogenoallylthio having in each case from 1 to 3 halogen atoms, cyano, nitro, $C_1$–$C_3$-alkyl, $C_1$–$C_3$-alkoxy and halogen, characterized in that a compound of the formula (II)

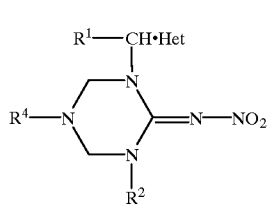

(II)

in which $R^1$, $R^2$ and Het are as defined above, and $R^4$ is $C_1$–$C_{10}$-alkyl, $C_3$–$C_6$-cycloalkyl, phenyl, benzyl or heterocyclylmethyl, each of which may be unsubstituted or substituted, where heterocyclyl is an unsaturated or saturated 5- or 6 -membered heterocycle containing one or two (preferably one) heteroatoms from the series nitrogen, oxygen and sulphur, such as, for example, furan, tetrahydrofuran, thiophene or pyridine, is reacted with urea in the presence of a diluent.

The compounds of the formula (I) can also be in the form of double-bond isomers as regards the —N═C(2) bond and in their tautomeric forms (formulae Ia, Ib):

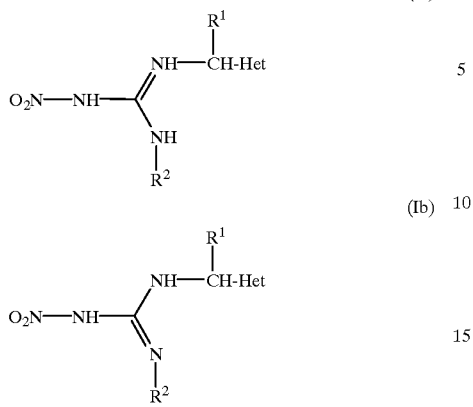

Formula (I) is accordingly to be taken to mean that it also includes the corresponding double-bond isomers and the formulae (Ia) and (Ib).

Surprisingly, the process according to the invention produces, selectively and in high yields, the end-products of the formula (I) in pure form after a short reaction time under mild reaction conditions.

For example, using1-(2-chlorothiazol-5-ylmethyl)-2-nitro-imino-3,5-dimethyl-1,3,5-triazacyclohexane as starting material, the course of the process according to the invention can be shown by the following equation:

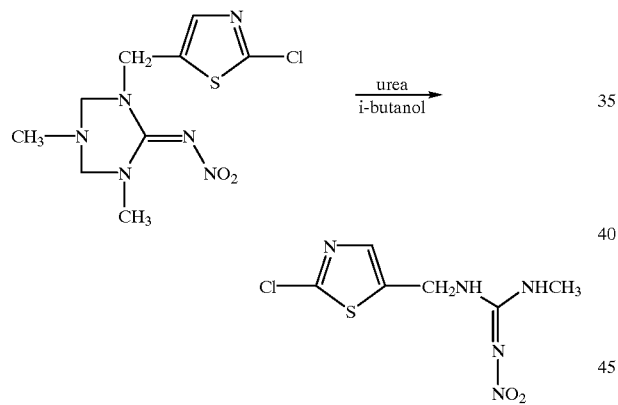

The compounds required as starting materials for the process according to the invention are generally defined by the formula (II).

Preferred substituents and ranges of the radicals listed in the formulae mentioned above and below are illustrated below:

$R^1$ is preferably hydrogen, methyl, ethyl, n- or i-propyl, $R^2$ is preferably hydrogen, methyl, ethyl, n-propyl, i-propyl or n-butyl, cyclopropyl, cyclopentyl, cyclohexyl or a radical —$CH_2R^3$, $R^3$ is preferably $C_2-C_5$-alkenyl, $C_2-C_5$-alkinyl, phenyl, cyanophenyl, nitrophenyl, halogenophenyl having from 1 to 3 halogen atoms, phenyl substituted by $C_1-C_3$-alkyl, $C_1-C_3$-halogenoalkyl having from 1 to 7 halogen atoms, $C_1-C_3$-alkoxy or $C_1-C_3$-halogenoalkoxy having from 1 to 7 halogen atoms, 3-pyridyl, 5-thiazolyl, 5-thiazolyl substituted by one to two (preferably one) substituents from the group consisting of $C_1-C_3$-alkyl, $C_1-C_3$-halogenoalkyl having from 1 to 7 halogen atoms, cyclopropyl, halogenocyclopropyl having from 1 to 3 halogen atoms, $C_2-C_3$-alkenyl, $C_2-C_3$-alkinyl, $C_1-C_3$-alkoxy, $C_2-C_3$-halogenoalkenyl and $C_2-C_3$-halogenoalkinyl having in each case from 1 to 4 halogen atoms, $C_1-C_3$-halogenoalkoxy having from 1 to 7 halogen atoms, $C_1-C_3$-alkylthio, $C_1-C_3$-halogenoalkylthio having from 1 to 7 halogen atoms, allyloxy, propargyloxy, allylthio, propargylthio, halo-genoallyloxy and halo-genoallylthio having in each case from 1 to 3 halogen atoms, halogen, cyano and nitro; or 3-pyridyl substituted by one to two (preferably one) radicals from the group consisting of $C_1-C_3$-halogenoalkyl having from 1 to 7 halogen atoms, cyclopropyl, halogenocyclopropyl having from 1 to 3 halogen atoms, $C_2-C_3$-alkenyl, $C_2-C_3$-alkinyl, $C_2-C_3$-halogenoalkenyl and $C_2-C_3$-halogenoalkinyl having in each case from 1 to 4 halogen atoms, $C_1-C_3$-halogenoalkoxy having from 1 to 7 halogen atoms, $C_1-C_3$-alkylthio, $C_1-C_3$-halogenoalkylthio having from 1 to 7 halogen atoms, allyloxy, propargyloxy, allylthio, propargylthio, halo-genoallyloxy and halogenoallylthio having in each case from 1 to 3 halogen atoms, cyano, nitro, $C_1-C_3$-alkyl, $C_1-C_3$-alkoxy and halogen, $R^4$ is preferably $C_1-C_{10}$-alkyl, $C_3-C_6$-cycloalkyl, $C_1-C_{10}$-alkyl substituted by from 1 to 12 radicals from the group consisting of halogen, hydroxyl, $C_1-C_4$-alkoxy, $C_1-C_4$-halogenoalkoxy having from 1 to 9 halogen atoms, di-($C_1-C_4$-alkyl)-amino and $C_1-C_5$-alkoxycarbonyl, $C_3-C_6$-cycloalkyl substituted by from 1 to 4 radicals from the series $C_1-C_4$-alkyl and halogen, phenyl, benzyl, or phenyl or benzyl in each case substituted by from 1 to 3 ring substituents from the group consisting of halogen, $C_1-C_4$-alkyl, $C_1-C_4$-halogenoalkyl having from 1 to 9 halogen atoms, $C_1-C_4$-alkoxy, $C_1-C_4$-halogenoalkoxy having from 1 to 9 halogen atoms, $C_1-C_4$-alkylthio, nitro and cyano, or heterocyclylmethyl where heterocyclyl is an unsaturated or saturated 5- or 6-membered heterocycle having one or two (preferably one) heteroatoms from the series nitrogen, oxygen and sulphur, such as, for example, furan, tetrahydrofuran, thiophene or pyridine, Het is preferably an unsubstituted or mono- or disubstituted (preferably monosubstituted) heterocyclic radical from the series

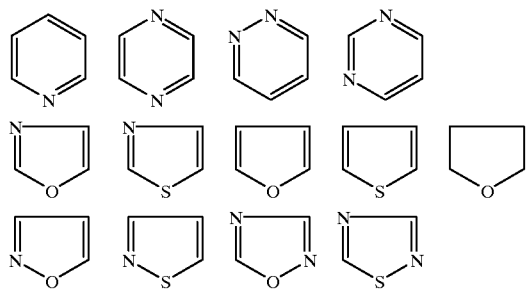

the substituents preferably being chosen from the series fluorine, chlorine, bromine, methyl, ethyl, methoxy and ethoxy, $R^1$ is particularly preferably hydrogen or methyl, $R^2$ is particularly preferably hydrogen, methyl, ethyl, n-propyl, i-propyl, n-butyl, cyclopropyl, cyclopentyl, cyclohexyl or a radical —$CH_2R^3$, $R^3$ is particularly preferably $C_2-C_3$-alkenyl, $C_2-C_3$-alkinyl, phenyl, cyanophenyl, nitrophenyl, halogenophenyl having from 1 to 3 halogen atoms, phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms, 3-pyridyl, 5-thiazolyl, 5-thiazolyl or 3-pyridyl each substituted by one or two (preferably one) substituents from the group consisting of $C_1$–$C_3$-alkyl, $C_1$–$C_3$-halogenoalkyl having from 1 to 7 halogen atoms, $C_1$–$C_3$-alkoxy, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, halogen, cyano and nitro, $R^4$ is particularly preferably $C_1$–$C_{10}$-alkyl, $C_3$–$C_6$-cycloalkyl, $C_1$–$C_8$-alkyl, substituted by from 1 to 6 radicals from the group consisting of halogen, $C_1$–$C_4$-alkoxy and $C_1$–$C_4$-halogenoalkoxy having in each case from 1 to 9 halogen atoms, $C_3$–$C_6$-cycloalkyl substituted by 1 or 2 radicals from the series methyl, ethyl, fluorine or chlorine, phenyl, benzyl, or phenyl or benzyl each substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro and cyano, or heterocyclylmethyl, where heterocyclyl is an unsaturated or saturated 5- or 6-membered heterocycle containing one heteroatom from the series nitrogen, oxygen and sulphur, such as, for example, furan, tetrahydrofuran, thiophene or pyridine, Het is particularly preferably thiazolyl, pyridyl or tetrahydrofuranyl, each of which may be unsubstituted or mono- or disubstituted (in particular monosubstituted), the substituents being chosen from the series fluorine, chlorine, methyl and methoxy (in particular chlorine), Halogen (atoms) are preferably and particularly preferably fluorine (atoms), chlorine (atoms) and bromine (atoms), $R^1$ is very particularly preferably hydrogen or methyl, especially hydrogen, $R^2$ is very particularly preferably hydrogen, methyl, ethyl, n-propyl, cyclopropyl, cyclopentyl, allyl or propargyl, $R^4$ is very particularly preferably methyl, ethyl, n-propyl, cyclopropyl, cyclopentyl, cyclohexyl, phenyl, benzyl or furfurylmethyl, Het is very particularly preferably one of the radicals

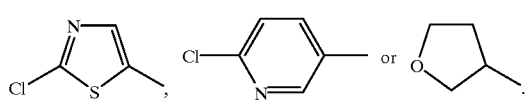

Particularly preferred starting materials for the process according to the invention are compounds of the formula (IIa)

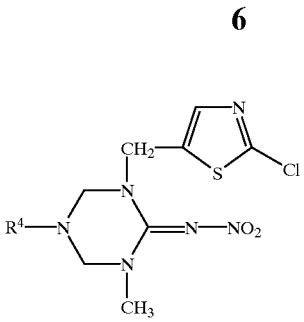

in which $R^4$ is methyl, ethyl, cyclopropyl, cyclopentyl, benzyl or furfurylmethyl, where, of these, methyl, benzyl and furfurylmethyl are in turn preferred.

Particularly preferred starting materials for the process according to the invention are compounds of the formula (IIb) and (IIc)

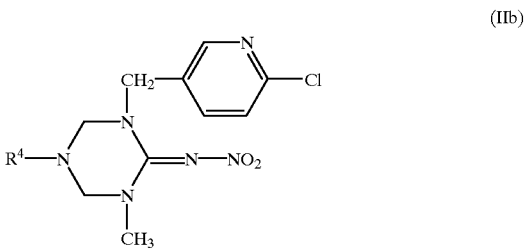

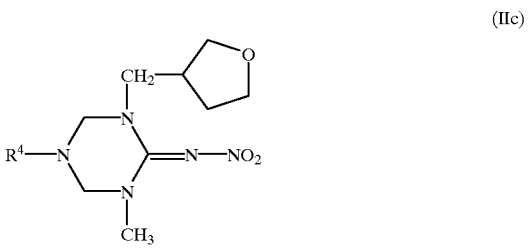

in which $R^4$ is as defined for the compounds of the formula (IIa).

The end-products of the process according to the invention are, when compounds of the formula (IIa) are used, the following compound

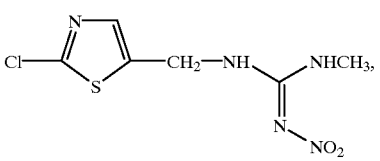

and when the compound of the formula (IIc) is used, the following compound

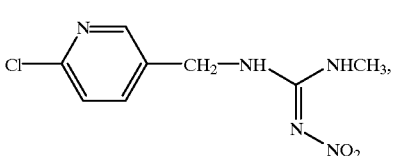

and when the compound of the formula (IIc) is used, the following compound

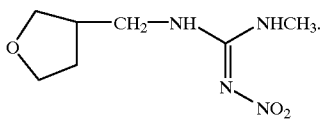

The radical definitions and explanations given in general terms above or listed in the preferred ranges can be combined with one another as desired, i.e. also between the respective ranges and preferred ranges. They apply to the end-products and also to the precursors and intermediates.

Preference is given to using those compounds of the formula (II) which have a combination of the preferred meanings given above in the process according to the invention.

Particular preference is given to using those compounds of the formula (II) which have a combination of the particularly preferred meanings given above in the process according to the invention.

Very particular preference is given to using those compounds of the formula (II) which have a combination of the very particularly preferred meanings given above in the process according to the invention.

The starting materials of the formula (II) are known or can be prepared by known processes (cf. EP-A-0 483 062, JP-03 291 267, EP-A-0 483 055, EP-A-0 428 941, EP-A-0 386 565).

The compounds of the formula (II) are, for example, obtained when a) a compound of the formula (III)

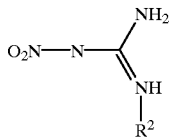

(III)

is reacted with formaldehyde and a compound of the formula (IV)

$$H_2N—R^4 \quad (IV)$$

and b) the resulting compound of the formula (V)

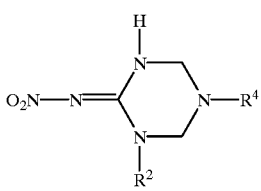

(V)

is reacted with a compound of the formula (VI)

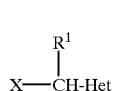

(VI)

where, in the formulae (II) to (VI), the radicals $R^1$, $R^2$, $R^4$ and Het are as defined above, and X is a leaving group.

Examples of suitable leaving group X are: halogen, preferably chlorine, bromine or iodine, or sulphonic acid radicals, such as alkyl sulphonic acid radicals, for example, mesylate or tosylate.

Stage a) of the above process for the preparation of the compounds of the formula (II) is advantageously carried out under atmospheric pressure, optionally also under increased pressure in an inert solvent and at temperatures between 0° C. and +140° C., preferably between +20° C. and +120° C. Particularly suitable solvents are alcohols, such as methanol, ethanol and propanol, and also water. Other suitable solvents are, for example, aromatic hydrocarbons, such as benzene, toluene or xylene; ethers, such as tetrahydroftiran, dioxane or diethyl ether; halogenated hydrocarbons, such as methylene chloride, chloroform, tetrachloromethane or chlorobenzene or other solvents which do not impair the reaction. The solvents can also be used as mixtures. Process stage b) can preferably be carried out under atmospheric or slightly increased pressure and in the presence of, preferably, aprotic solvents or diluents. Suitable solvents or diluents are, for example, ethers or ether-like compounds, such as diethyl ether, dipropyl ether, dibutyl ether, dioxane, dimethoxy ether and tetrahydrofuran; aliphatic, aromatic and halogenated hydrocarbons, in particular benzene, toluene, xylene, chloroform, methylene chloride, tetrachloromethane or chlorobenzene; nitriles, such as acetonitrile or propionitrile; dimethyl sulphoxide or dimethylformamide and also mixtures of these solvents. This process stage is generally carried out at a temperature of from −20° C. to +140° C., preferably between 0° C. and +120° C., preferably in the presence of a base. Suitable bases are, for example, carbonates, such as sodium carbonate or potassium carbonate. Hydrides, such as sodium hydride, potassium hydride or calcium hydride, can also be used as bases. The reaction can optionally also be carried out in the presence of a catalyst, e.g. caesium chloride.

The starting materials of the above formulae (IV) and (VI) are known and available commercially or can be readily prepared by analogy with known processes. The 2-nitroguanidine starting materials of the formula (III) are likewise known; they can be prepared advantageously from S-methyl-N-nitroisothiourea by reaction with a corresponding primary amine (cf. U.S. Pat. No. 4,804,780 and 4,221, 802). N-Methyl-N'-nitroguanidine can also be obtained by reacting nitroguanidine with methylamine (cf. EP-A-0 798 293 of the Applicant). S-Methyl-N-nitroisothiourea can be obtained in good yield by nitration of S-methylisothiourea (cf. J. Am. Soc. 76, 1877 (1954)).

The process according to the invention is carried out in the presence of a diluent.

Particularly suitable diluents are organic solvents, especially polar protic solvents, for example alcohols, such as methanol, ethanol, n-propanol, i-propanol, n-butanol or i-butanol and polar aprotic solvents, for example amides, such as dimethyl formamide, dimethylacetamide or N-methylpyrrolidone, or sulphoxides such as dimethylsulphoxide.

9

It is also possible to use mixtures of the specified diluents. Particularly suitable diluents are alcohols, in particular those mentioned above.

It may be advantageous to add another solvent to the reaction mixture. Suitable solvents are ethers, for example dibutyl ether, tetrahydrofuran, dioxane, glycoldimethylether or diglycoldimethylether, and also hydrocarbons, such as benzene, toluene or xylene, halogenated hydrocarbons, such as methylene chloride, chloroform, tetrachloromethane, chlorobenzene or o-dichlorobenzene, nitrites, such as acetonitrile, carboxylic esters, such as ethyl acetate or also ketones, such as acetone or methyl isopropyl ketone.

It is also possible to use mixtures of the specified solvents. Ethers are preferably used.

The process according to the invention is carried out at temperatures between 0° C. and 200° C., preferably between 40° C. and 150° C.

The process is preferably carried out under atmospheric pressure.

The urea is generally used in a molar ratio of from 1:10 to 10:1, preferably 1:4 to 4:1, in particular 1:1 to 3:1, based on the starting compound of the formula (II).

The reaction is generally carried out by heating the starting material of the formula (II) and urea in the diluent and optionally in a solvent, to the desired temperature.

To work-up, after cooling, water is added, and the end-product, optionally after evaporating the mixture, is isolated, for example by filtration or extraction.

It is also possible to work up the reaction mixture without water by, when the reaction is complete, distilling off the diluent and the solvent where appropriate and extracting the residue which remains with a suitable extractant. Suitable extractants are, in principle, all solvents which are inert with respect to the end-products and in which the end-products are sufficiently soluble.

Examples thereof include aliphatic hydrocarbons, such as n-pentane, n-hexane, cyclohexane, halogenated aliphatic hydrocarbons, such as methylene chloride or chloroform, aromatic hydrocarbons, such as benzene, toluene or xylene, halogenated aromatic hydrocarbons, such as chlorobenzene or o-dichlorobenzene or else ethers, such as, for example, methyl tert-butyl ether.

The end-products crystallize out, optionally after evaporating off the extractant, and can be isolated by filtration, or the extractant is completely or virtually completely removed and, if necessary, the residue is purified, for example by recrystallization.

The reaction is preferably carried out in a diluent from which, when the reaction mixture is cooled, the end-product can crystallize out and can be isolated in a simple manner, for example by filtration.

Suitable diluents are alcohols, in particular isobutanol.

The compounds for the of the formula (I) prepared according to the invention are useful active ingredients in pest control. In particular, the compounds of the formula (I) are suitable for controlling insects and arachnids, which are encountered in useful and ornamental plants in agriculture, in particular, cotton, vegetable and fruit plantations, in forests, in the protection of stored products and materials and in the hygiene sector, in particular on pets and useful animals (see e.g. EP-A-0 376 279, EP-A-0 375 907, EP-A-0 383 091).

10

Example 1

Preparation of

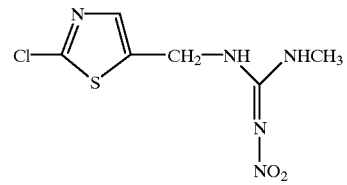

1-(2-chlorothiazol-5-ylmethyl)-2-nitro-3-methylguanidine a) 3 g of 1-(2-chlorothiazol-5-ylmethyl)-2-nitroimino-3, 5-dimethyl-1,3,5-triaza-cyclohexane of the formula (for preparation see EP-A-0 428 941)

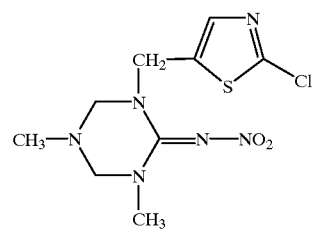

and 1.2 g of urea ($H_2N$—CO—$NH_2$) are suspended in 30 ml of dimethoxyethane and, after 10 ml of isobutanol have been added, are refluxed for 9 hours. The mixture is added to dilute aqueous sodium chloride solution, the suspension is somewhat concentrated by evaporation under reduced pressure, and the solid is filtered off with suction, washed with water and dried.

Yield: 2.0 g HPLC purity>98%.

$^1$H-NMR (DMSO-$d_6$), δ=2.8 ppm (3H, s); 4.5 ppm (2H, s), 7.6 ppm (1H, s), 7.9–8.1 ppm (1H, broad), 9.1–9.3 ppm (1H, broad).

According to its chromatographic and spectroscopic data, the product is identical to an authentic sample of 1-(2-chlorothiazol-5-ylmethyl)-2-nitro-3-methylguanidine obtained by another route.

b) 3 g of the same starting compound as in Example 1a) and 1.2 g of urea are refluxed in 30 ml of isobutanol for 6 hours. After the mixture has been cooled, 200 ml of water are added, and the isobutanol is distilled off azeotropically under reduced pressure. The solid which precipitates out is filtered off with suction and dried.

Yield: 2.1 g (86% of theory).

Analytical data as in 1a); HPLC purity>99%.

c) 15 g of the starting compound as in Example 1a) and 6.0 g of urea are refluxed in 100 ml of isobutanol for 8 hours. The mixture is left to cool, and the solid formed is filtered off, then washed with a small amount of isobutanol and dried.

Yield: 10.2 g (84% of theory). Analytical purity as in 1b).

d) 1 g of 1-(2-chlorothiazol-5-ylmethyl)-2-nitroimino(3-methyl-5-benzyl)-1,3,5-triazacyclohexane (preparation EP-A-0 483 055) and 0.3 g of urea are refluxed in 10 ml of isobutanol for 10 hours. Work-up as in b) gives 0.4 g of the above compound.

e) 135 kg of 1-(2-chlorothiazol-5-ylmethyl)-2-nitroimino-3-methyl-5-benzyl-1,3,5-triazacyclohexane of the formula

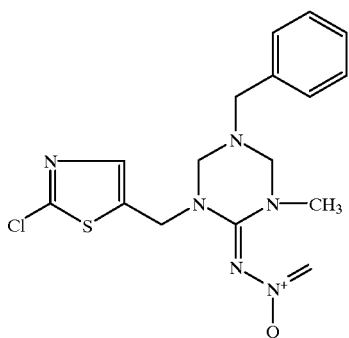

and 53 kg of urea are heated at 100° C. in 585 kg of isobutanol for 12 hours. The mixture is cooled to 20° C. and crystallized, and the crystals are isolated by filtration. The crystals are washed with water and then dried to give 75 kg of 1-(2-chlorothiazol-5-ylmethyl)-2-nitro-3-methylguanidine.

Using a similar method, it is also possible to obtain the compounds of the formula (I) given in the table below:

TABLE

| Example No. | Het | $R^1$ | $R^2$ |
|---|---|---|---|
| 2 | 2-chloropyridin-5-yl | H | H |
| 3 | 2-chloropyridin-5-yl | H | —CH$_3$ |
| 4 | 2-chloropyridin-5-yl | H | —C$_2$H$_5$ |
| 5 | 2-chloropyridin-5-yl | H | —C$_3$H$_7$(n) |
| 6 | 2-chloropyridin-5-yl | H | cyclopropyl |
| 7 | 2-chloropyridin-5-yl | H | —C$_4$H$_9$(n) |
| 8 | 2-chloropyridin-5-yl | H | —CH(CH$_3$)$_2$ |
| 9 | 2-chloropyridin-5-yl | H | —CH$_2$-phenyl |
| 10 | 2-chloropyridin-5-yl | H | —CH$_2$-(pyridin-3-yl) |

TABLE-continued

| Example No. | Het | R¹ | R² |
| --- | --- | --- | --- |
| 11 | 2-chloro-5-pyridyl | H | —CH₂-(2-chloro-5-pyridyl) |
| 12 | 2-chloro-5-pyridyl | H | —CH₂-(4-chlorophenyl) |
| 13 | 2-chloro-5-pyridyl | —CH₃ | —CH₃ |
| 14 | 2-chloro-5-pyridyl | —CH₃ | —C₂H₅ |
| 15 | 2-chloro-5-pyridyl | —CH₃ | cyclopropyl |
| 16 | 2-chloro-5-pyridyl | —CH₃ | —C₃H₇(n) |
| 17 | 2-chloro-5-pyridyl | —C₂H₅ | —CH₃ |
| 18 | 2-chloro-5-pyridyl | —C₂H₅ | —C₂H₅ |
| 19 | 2-chloro-5-pyridyl | —C₂H₅ | cyclopropyl |
| 20 | 2-chloro-5-thiazolyl | H | H |
| 21 | 2-chloro-5-thiazolyl | H | CH₃ |
| 22 | 2-chloro-5-thiazolyl | H | —C₂H₅ |

TABLE-continued
| Example No. | Het | R¹ | R² |
|---|---|---|---|
| 23 | 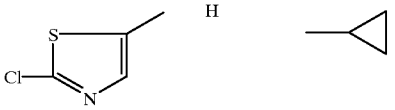 | H |  |
| 24 | 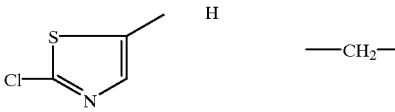 | H | —CH₂—C₆H₅ |
| 25 | 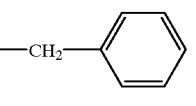 | H | —CH₂—C₆H₄—Cl |
| 26 | 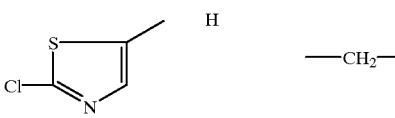 | CH₃ | CH₃ |
| 27 | 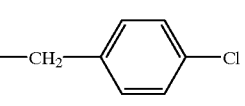 | C₂H₅ | CH₃ |
| 28 | 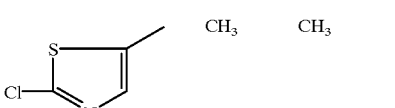 | CH₃ | C₂H₅ |
| 29 | 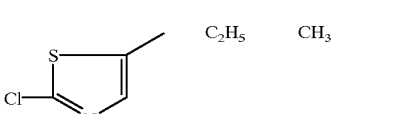 | CH₃ | 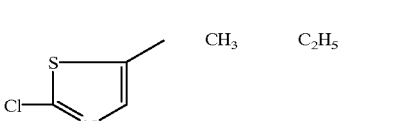 |
| 30 | 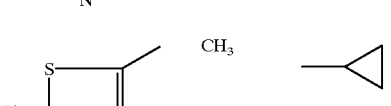 | H | —CH₂—CH=CH₂ |
| 31 |  | H | —CH₂—C≡CH |
| 32 | 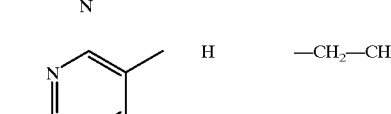 | H | —CH₂—CH=CH₂ |
| 33 | 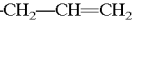 | H | —CH₂—C≡CH |
| 34 | 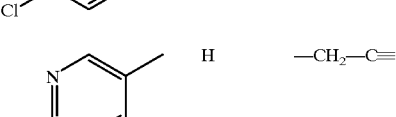 | H | CH₃ |
| 35 | 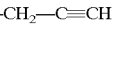 | CH₃ | CH₃ |

Preparation of novel starting compounds:

EXAMPLE ((V-1))

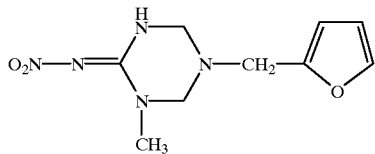

A mixture of N-methylnitroguanidine (98.3 g, 0.5 mol, water content 40%) and 37% strength aqueous formaldehyde solution (200 ml, 2.7 mol) is stirred at 70° C. for 1 hour. Then, at this temperature, a solution of furfurylamine (51 g, 0.53 mol) in water (50 g) is added. The mixture is then stirred for 2 hours at 70° C. and then cooled to 30° C. At this temperature, a few seed crystals are added, the mixture is cooled to 20° C., and the precipitate is filtered off with suction, washed with water and dried.

Yield: 104 g (87% of theory)

EXAMPLE (II-1)

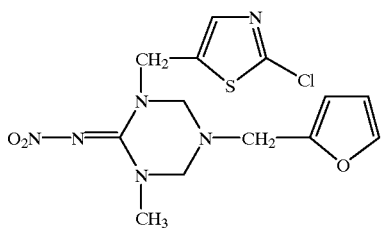

To the mixture of 48 g (0.2 mol) of the compound according to Example (V-1), 36 g (0.26 mol) of ground potassium carbonate and 100 ml of dimethylformamide is added, at 50° C., 33.6 g (0.2 mol) of 2-chloro-5-chloromethylthiazole, and the mixture is stirred for 16 hours at this temperature. The mixture is left to cool, added to water, rendered approximately neutral using sulphuric acid and filtered with suction, and the product is washed with water and dried.

What is claimed is:

1. A process for the preparation of compounds of the formula (I)

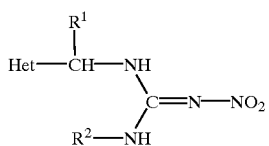

(I)

in which
R$^1$ is hydrogen or $C_1$–$C_4$-alkyl,
R$^2$ is hydrogen, $C_1$–$C_6$-alkyl, $C_3$–$C_6$-cycloalkyl or a radical —CH$_2$R$^3$,
R$^3$ is $C_2$–$C_5$-alkenyl;
$C_2$–$C_5$-alkinyl;
phenyl;
cyanophenyl;
nitrophenyl;
halogenophenyl having from 1 to 3 halogen atoms;
phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms;
3-pyridyl;
5-thiazolyl;
5-thiazolyl substituted by one to two substituents from the group consisting of $C_1$–$C_3$-alkyl, $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_1$–$C_3$-alkoxy, $C_2$–$C_3$-halogenoalkenyl and $C_2$–$C_3$-halogenoalkinyl having in each case from 1 to 4 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy and halogenoallylthio having in each case from 1 to 3 halogen atoms, halogen, cyano, nitro;
3-pyridyl substituted by one to four radicals from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl and $C_2$–$C_3$-halogenoalkinyl having in each case from 1 to 4 halogen atoms; $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy and halogenoallylthio having in each case from 1 to 3 halogen atoms, cyano, nitro, $C_1$–$C_3$-alkyl, $C_1$–$C_3$-alkoxy, halogen;

Het is an unsubstituted or substituted heterocyclic radical selected the group consisting of

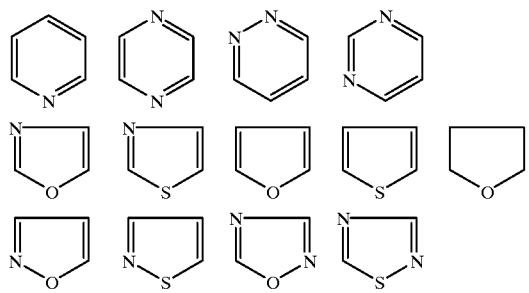

which may include one to two substituents from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl and $C_2$–$C_3$-halogenoalkinyl having from 1 to 4 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy, halogenoallylthio, cyano, nitro, $C_1$–$C_3$-alkyl, $C_1$–$C_3$-alkoxy, and halogen, comprising reacting a compound of the formula (II)

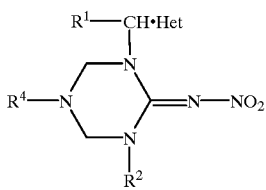

(II)

in which
R¹, R² and Het are as defined above, and
R⁴ is $C_1$–$C_{10}$-alkyl, $C_3$–$C_6$-cycloalkyl, phenyl, benzyl or heterocyclylmethyl, each of which may be unsubstituted or substituted, where heterocyclyl is an unsaturated or saturated 5- or 6-membered heterocycle containing one or two heteroatoms from the series nitrogen, oxygen and sulphur,
with urea in the presence of a diluent.

2. The process of claim 1, in which
R¹ is hydrogen, methyl, ethyl, n- or i-propyl,
R² is hydrogen, methyl, ethyl, n-propyl, i-propyl or n-butyl, cyclopropyl, cyclopentyl, cyclohexyl or a radical —$CH_2R^3$,
R³ is $C_2$–$C_5$-alkenyl;
$C_2$–$C_5$-alkinyl;
phenyl;
cyanophenyl;
nitrophenyl;
halogenophenyl having from 1 to 3 halogen atoms;
phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms;
3-pyridyl;
5-thiazolyl;
5-thiazolyl substituted by one to two substituents from the group consisting of $C_1$–$C_3$-alkyl, $C_1$–$C_3$halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_1$–$C_3$-alkoxy, $C_2$–$C_3$-halogenoalkenyl and $C_2$–$C_3$-halogenoalkinyl having from 1 to 4 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy and halogenoallylthio having in each case from 1 to 3 halogen atoms, halogen, cyano, nitro;
3-pyridyl substituted by one to two radicals form the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl and $C_2$–$C_3$-halogenoalkinyl having in each case from 1 to 4 halogen atoms, $C_1$–$C_3$-halogenalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy and halogenoallylthio having in each case from 1 to 3 halogen atoms, cyano, nitro, $C_1$–$C_3$-alkyl, $C_1$–$C_3$-alkoxy, halogen;
R⁴ is $C_1$–$C_{10}$-alkyl;
$C_3$–$C_6$-cycloalkyl;
$C_1$–$C_{10}$-alkyl substituted by from 1 to 12 radicals from the group consisting of halogen, hydroxyl, $C_1$–$C_4$-alkoxy, $C_1$–$C_4$-halogenoalkoxy having from 1 to 9 halogen atoms, di-($C_1$–$C_4$-alkyl)-amino and $C_1$–$C_5$-alkoxycarbonyl;
$C_3$–$C_6$-cycloalkyl substituted by from 1 to 4 radicals from the series $C_1$–$C_4$-alkyl and halogen,
phenyl;
benzyl;
or phenyl or benzyl or heterocyclylmethyl, in each case substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro, and cyano; where heterocyclyl is an unsaturated or saturated 5- or 6-membered heterocycle having one or two heteroatoms from the series nitrogen, oxygen and sulphur,
Het is an unsubstituted or mono- or di-substituted heterocyclic radical from the series

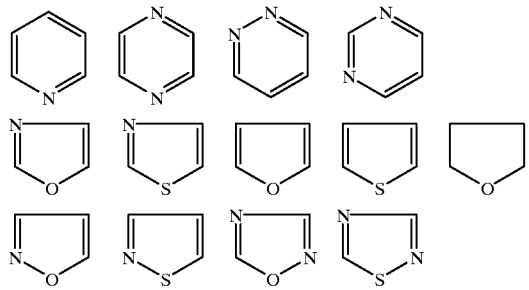

the substituents being chosen from the series fluorine, chlorine, bromine, methyl, ethyl, methoxy and ethoxy.

3. The process of claim 1, in which
R¹ is hydrogen or methyl,
R² is hydrogen, methyl, ethyl, n-propyl, i-propyl, n-butyl, cyclopropyl, cyclopentyl, cyclohexyl or a radical —$CH_2R^3$,
R³ is $C_2$–$C_3$-alkenyl;
$C_2$–$C_3$-alkinyl
phenyl;
cyanophenyl;
nitrophenyl;
halogenophenyl having from 1 to 3 halogen atoms;
phenyl substituted by $C_1$–$C_3$-alkyl, $C_1$–$C_3$-halogenoalkyl having from 1 to 7 halogen atoms, or $C_1$–$C_3$-alkoxy or $C_1$–$C_3$-halogenoalkoxy having from 1 to 7 halogen atoms,
3-pyridyl;
5-thiazolyl;
5-thiazolyl or 3-pyridyl each substituted by one or two substituents from the group consisting of $C_1$–$C_3$-alkyl, $C_1$–$C_3$-halogenoalkyl having from 1 to 7 halogen atoms, $C_1$–$C_3$-alkoxy, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, halogen, cyano, and nitro,
R⁴ is $C_1$–$C_{10}$-alkyl;
$C_3$–$C_6$-cycloalkyl;
$C_1$–$C_8$-alkyl substituted by from 1 to 6 radicals from the group consisting of halogen, $C_1$–$C_4$-alkoxy and $C_1$–$C_4$-halogenoalkoxy having in each case from 1 to 9 halogen atoms;

$C_3$–$C_6$-cycloalkyl substituted by 1 or 2 radicals from the series methyl, ethyl, fluorine or chlorine;

phenyl;

benzyl;

phenyl or benzyl or heterocyclylmethyl each substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro and cyano;

or heterocyclyl-methyl, where heterocyclyl is an unsaturated or saturated 5- or 6-membered heterocycle containing one heteroatom from the series nitrogen, oxygen and sulphur, Het is thiazolyl, pyridyl or tetrahydrofuranyl, each of which may be unsubstituted or mono- or disubstituted, the substituents being chosen from the series fluorine, chlorine, methyl and methoxy.

4. The process of claim 1, in which $R^1$ is hydrogen or methyl, $R^2$ is hydrogen, methyl, ethyl, n-propyl, cyclopropyl, cyclopentyl, allyl or propargyl, $R^4$ is methyl, ethyl, n-propyl, cyclopropyl, cyclopentyl, phenyl, benzyl or furfuryl, Het is one of the radicals

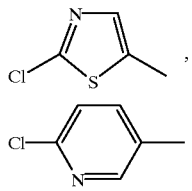

-continued

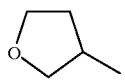

5. The process of claim 1 wherein $R^4$ is heterocyclylmethyl where heterocyclyl is furan, tetrahydrofuran, thiophene or pyridine.

6. The process of claim 2 wherein $R^4$ is heterocyclylmethyl where heterocyclyl is furan, tetrahydrofuran, thiophene or pyridine.

7. The process of claim 3 wherein $R^4$ is heterocyclylmethyl where heterocyclyl is furan, tetrahydrofuran, thiophene or pyridine.

8. Compound of the formula

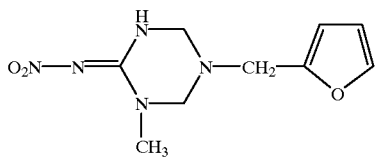

9. Compound of the formula

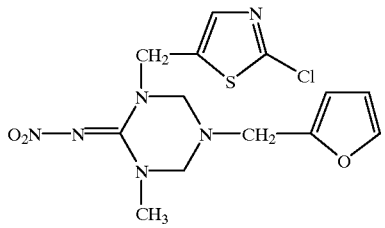

* * * * *